US009969570B2

(12) United States Patent
Heise et al.

(10) Patent No.: US 9,969,570 B2

(45) Date of Patent: May 15, 2018

(54) SYSTEM FOR TRANSPORTING CONTAINERS BETWEEN DIFFERENT STATIONS AND A CONTAINER CARRIER

(71) Applicant: Roche Diagnostics Operations, Inc., Indianapolis, IN (US)

(72) Inventors: Michael Heise, Marbach (DE); George Teodorescu, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days. days.

(21) Appl. No.: 13/649,224

(22) Filed: Oct. 11, 2012

(65) Prior Publication Data

US 2013/0034410 A1 Feb. 7, 2013

Related U.S. Application Data

(63) Continuation of application No. PCT/EP2011/057344, filed on May 6, 2011.

(30) Foreign Application Priority Data

May 7, 2010 (DE) ........................ 10 2010 028 769

(51) Int. Cl.
*B65G 54/02* (2006.01)
*B65G 1/137* (2006.01)
(Continued)

(52) U.S. Cl.
CPC ............. *B65G 54/02* (2013.01); *B65G 1/137* (2013.01); *G01N 35/04* (2013.01); *B65G 1/0478* (2013.01);
(Continued)

(58) Field of Classification Search
CPC ........... B65G 54/02; G01N 2035/0477; G01N 2035/0491
See application file for complete search history.

(56) References Cited

U.S. PATENT DOCUMENTS 3,273,727 A 9/1966 Rogers et al.
3,653,485 A 4/1972 Donlon
(Continued)

FOREIGN PATENT DOCUMENTS

CN 201045617 Y 4/2008
CN 102109530 A 6/2011
(Continued)

OTHER PUBLICATIONS

International Search Report issued Sep. 6, 2011 in Application No. PCT/EP2011/057344, 3 pages.
(Continued)

*Primary Examiner* — P. Kathryn Wright
(74) *Attorney, Agent, or Firm* — Roche Diagnostics Operations, Inc.

(57) ABSTRACT

A system for transporting containers between different stations is presented. The containers are accommodated in container carriers. The system comprises a control unit for controlling the transport of the container carriers, a transport area divided into subareas and on which the container carriers can be movably arranged, and a drive. The drive is activated by the control unit and each subarea is assigned a respective drive. Each drive applies a drive force to an associated container carrier.

11 Claims, 2 Drawing Sheets

100 22 30 52 51 30 53 23 10 30 52 51 50 21 10 30 54 10 30 55 56 51 52 20 53 51 52 53

(51) Int. Cl.
*G01N 35/04* (2006.01)
*B65G 1/04* (2006.01)

(52) U.S. Cl.
CPC .................. *B65G 2203/046* (2013.01); *G01N 2035/0406* (2013.01); *G01N 2035/0477* (2013.01); *G01N 2035/0491* (2013.01)

(56) References Cited

U.S. PATENT DOCUMENTS 3,901,656 A 8/1975 Durkos et al.
4,150,666 A 4/1979 Brush
4,395,164 A 7/1983 Beltrop
4,544,068 A 10/1985 Cohen
4,771,237 A 9/1988 Daley
5,120,506 A 6/1992 Saito et al.
5,295,570 A 3/1994 Grechsch et al.
5,309,049 A 5/1994 Kawada et al.
5,523,131 A 6/1996 Isaacs et al.
5,530,345 A 6/1996 Murari et al.
5,636,548 A 6/1997 Dunn et al.
5,641,054 A 6/1997 Mori et al.
5,651,941 A 7/1997 Stark et al.
5,720,377 A 2/1998 Lapeus et al.
5,735,387 A 4/1998 Polaniec et al.
5,788,929 A 8/1998 Nesti
6,045,319 A 4/2000 Uchida et al.
6,062,398 A 5/2000 Talmayr
6,141,602 A 10/2000 Igarashi et al.
6,151,535 A 11/2000 Ehlers
6,184,596 B1 2/2001 Ohzeki
6,191,507 B1 2/2001 Peltier et al.
6,206,176 B1 3/2001 Blonigan et al.
6,255,614 B1 7/2001 Yamakawa et al.
6,260,360 B1 7/2001 Wheeler
6,279,728 B1 8/2001 Jung et al.
6,293,750 B1 9/2001 Cohen et al.
6,429,016 B1 8/2002 McNeil
6,444,171 B1 9/2002 Sakazume et al.
6,571,934 B1 6/2003 Thompson et al.
7,028,831 B2 4/2006 Veiner
7,078,082 B2 7/2006 Adams
7,122,158 B2 10/2006 Itoh
7,278,532 B2 10/2007 Martin
7,326,565 B2 2/2008 Yokoi et al.
7,425,305 B2 9/2008 Itoh
7,428,957 B2 9/2008 Schaefer
7,578,383 B2 8/2009 Itoh
7,597,187 B2 10/2009 Bausenwein et al.
7,850,914 B2 12/2010 Veiner et al.
7,858,033 B2 12/2010 Itoh
7,875,254 B2 1/2011 Garton
7,939,484 B1 5/2011 Loeffler et al.
8,240,460 B1 8/2012 Bleau et al.
8,281,888 B2 10/2012 Bergmann
8,502,422 B2 8/2013 Lykkegaard
8,796,186 B2 8/2014 Shirazi
9,211,543 B2 12/2015 Ohga et al.
9,239,335 B2 1/2016 Heise
2002/0009391 A1 1/2002 Marquiss et al.
2003/0008958 A1 1/2003 Momoda et al.
2003/0089581 A1 5/2003 Thompson et al.
2003/0092185 A1 5/2003 Qureshi et al.
2004/0050836 A1 3/2004 Nesbitt et al.
2004/0084531 A1 5/2004 Itoh
2005/0061622 A1 3/2005 Martin
2005/0109580 A1 5/2005 Thompson
2005/0194333 A1 9/2005 Veiner et al.
2005/0196320 A1 9/2005 Veiner et al.
2005/0226770 A1 10/2005 Allen et al.
2005/0242963 A1 11/2005 Oldham et al.
2005/0247790 A1 11/2005 Itoh
2005/0260101 A1 11/2005 Nauck et al.
2005/0271555 A1 12/2005 Itoh
2006/0000296 A1 1/2006 Salter
2006/0047303 A1 3/2006 Ortiz et al.
2006/0219524 A1 10/2006 Kelly et al.
2007/0116611 A1 5/2007 DeMarco
2007/0210090 A1 9/2007 Sixt et al.
2007/0248496 A1 10/2007 Bondioli et al.
2007/0276558 A1 11/2007 Kim
2008/0012511 A1 1/2008 Ono
2008/0029368 A1 2/2008 Komori
2008/0056328 A1 3/2008 Rund et al.
2008/0131961 A1 6/2008 Crees et al.
2008/0286162 A1 11/2008 Onizawa et al.
2009/0004732 A1 1/2009 La Barre et al.
2009/0022625 A1 1/2009 Lee et al.
2009/0081771 A1 3/2009 Breidford et al.
2009/0128139 A1 5/2009 Drenth et al.
2009/0142844 A1 6/2009 LeComte
2009/0180931 A1 7/2009 Silbert et al.
2009/0322486 A1* 12/2009 Gerstel ........................ 340/10.1
2010/0000250 A1 1/2010 Sixt
2010/0152895 A1 6/2010 Dai
2010/0175943 A1 7/2010 Bergmann
2010/0186618 A1 7/2010 King et al.
2010/0255529 A1 10/2010 Cocola et al.
2010/0300831 A1 12/2010 Pedrazzini
2010/0312379 A1 12/2010 Pedrazzini
2011/0050213 A1 3/2011 Furukawa
2011/0124038 A1 5/2011 Bishop et al.
2011/0172128 A1 7/2011 Davies et al.
2011/0186406 A1 8/2011 Kraus
2011/0287447 A1 11/2011 Norderhaug et al.
2012/0037696 A1 2/2012 Lavi
2012/0129673 A1 5/2012 Fukugaki et al.
2012/0178170 A1 7/2012 Van Praet
2012/0211645 A1 8/2012 Tullo et al.
2012/0275885 A1 11/2012 Furrer et al.
2012/0282683 A1 11/2012 Mototsu
2012/0295358 A1 11/2012 Ariff et al.
2012/0310401 A1 12/2012 Shah
2013/0034410 A1 2/2013 Heise et al.
2013/0126302 A1 5/2013 Johns et al.
2013/0153677 A1 6/2013 Leen et al.
2013/0180824 A1 7/2013 Kleinikkink et al.
2013/0263622 A1 10/2013 Mullen et al.
2013/0322992 A1 12/2013 Pedrazzini
2014/0170023 A1 6/2014 Saito et al.
2014/0231217 A1 8/2014 Denninger et al.
2014/0234065 A1 8/2014 Heise et al.
2014/0234949 A1 8/2014 Wasson et al.
2014/0234978 A1 8/2014 Heise et al.
2015/0014125 A1 1/2015 Hecht
2015/0233956 A1 8/2015 Buehr
2015/0233957 A1 8/2015 Riether
2015/0241457 A1 8/2015 Miller
2015/0273468 A1 10/2015 Croquette et al.
2015/0273691 A1 10/2015 Pollack
2015/0276775 A1 10/2015 Mellars et al.
2015/0276776 A1 10/2015 Riether
2015/0276777 A1 10/2015 Riether
2015/0276778 A1 10/2015 Riether
2015/0276781 A1 10/2015 Riether
2015/0276782 A1 10/2015 Riether
2015/0360876 A1 12/2015 Sinz
2015/0360878 A1 12/2015 Denninger et al.
2016/0003859 A1 1/2016 Wenczel et al.
2016/0025756 A1 1/2016 Pollack et al.
2016/0054341 A1 2/2016 Edelmann
2016/0054344 A1 2/2016 Heise et al.
2016/0069715 A1 3/2016 Sinz
2016/0077120 A1 3/2016 Riether
2016/0097786 A1 4/2016 Malinkowski et al.
2016/0229565 A1 8/2016 Margner
2016/0274137 A1 9/2016 Baer
2016/0282378 A1 9/2016 Malinowski et al.
2016/0341750 A1 11/2016 Sinz et al.
2016/0341751 A1 11/2016 Huber et al.
2017/0059599 A1 3/2017 Riether
2017/0096307 A1 4/2017 Mahmudimanesh et al.
2017/0097372 A1 4/2017 Heise et al.
2017/0101277 A1 4/2017 Malinowski
2017/0108522 A1 4/2017 Baer

(56) References Cited

U.S. PATENT DOCUMENTS

| | | | |
|---|---|---|---|
| 2017/0131307 | A1 | 5/2017 | Pedain |
| 2017/0131309 | A1 | 5/2017 | Pedain |
| 2017/0131310 | A1 | 5/2017 | Volz et al. |
| 2017/0138971 | A1 | 5/2017 | Heise et al. |
| 2017/0160299 | A1 | 6/2017 | Schneider et al. |
| 2017/0168079 | A1 | 6/2017 | Sinz |
| 2017/0174448 | A1 | 6/2017 | Sinz |
| 2017/0184622 | A1 | 6/2017 | Sinz et al. |
| 2017/0248623 | A1 | 8/2017 | Kaeppeli et al. |
| 2017/0248624 | A1 | 8/2017 | Kaeppeli et al. |
| 2017/0363608 | A1 | 12/2017 | Sinz |

FOREIGN PATENT DOCUMENTS

| | | | | |
|---|---|---|---|---|
| DE | 3909786 | A1 | | 9/1990 |
| DE | 102012000665 | A1 | | 8/2012 |
| DE | 102011090044 | A1 | | 7/2013 |
| EP | 0601213 | A1 | | 6/1994 |
| EP | 0775650 | A1 | | 5/1997 |
| EP | 0896936 | A1 | | 2/1999 |
| EP | 0916406 | A2 | | 5/1999 |
| EP | 1122194 | A1 | | 8/2001 |
| EP | 2005-001055 | A | | 1/2005 |
| EP | 1524525 | A1 | | 4/2005 |
| EP | 2009-145188 | A | | 7/2009 |
| EP | 2119643 | A1 | | 11/2009 |
| EP | 2148117 | A1 | | 1/2010 |
| EP | 2327646 | A1 | | 6/2011 |
| EP | 2447701 | A2 | | 5/2012 |
| EP | 2500871 | A1 | | 9/2012 |
| EP | 2502675 | A1 | | 9/2012 |
| EP | 2887071 | A1 | | 6/2015 |
| GB | 2165515 | A | * | 4/1986 |
| JP | S56-147209 | A | | 11/1981 |
| JP | 60-223481 | A | | 11/1985 |
| JP | 61-081323 | A | | 4/1986 |
| JP | S61-069604 | A | | 4/1986 |
| JP | S61-094925 | A | | 5/1986 |
| JP | S61-174031 | A | | 8/1986 |
| JP | S61-217434 | A | | 9/1986 |
| JP | S62-100161 | A | | 5/1987 |
| JP | S63-31918 | A | | 2/1988 |
| JP | S63-48169 | A | | 2/1988 |
| JP | S63-82433 | U | | 5/1988 |
| JP | S63-290101 | A | | 11/1988 |
| JP | 01-148966 | A | | 6/1989 |
| JP | 01-266860 | A | | 10/1989 |
| JP | H02-87903 | A | | 3/1990 |
| JP | 03-192013 | A | | 8/1991 |
| JP | H03-38704 | Y2 | | 8/1991 |
| JP | H04-127063 | A | | 4/1992 |
| JP | H05-69350 | A | | 3/1993 |
| JP | H05-142232 | A | | 6/1993 |
| JP | H05-180847 | A | | 7/1993 |
| JP | 06-026808 | A | | 4/1994 |
| JP | 06-148198 | A | | 5/1994 |
| JP | 6156730 | A | | 6/1994 |
| JP | 06-211306 | A | | 8/1994 |
| JP | 07-228345 | A | | 8/1995 |
| JP | 07-236838 | A | | 9/1995 |
| JP | H07-301637 | A | | 11/1995 |
| JP | H09-17848 | A | | 1/1997 |
| JP | H11-083865 | A | | 3/1999 |
| JP | H11-264828 | A | | 9/1999 |
| JP | H11-304812 | A | | 11/1999 |
| JP | H11-326336 | A | | 11/1999 |
| JP | 2000-105243 | A | | 4/2000 |
| JP | 2000-105246 | A | | 4/2000 |
| JP | 3112393 | A | | 9/2000 |
| JP | 2001-124786 | A | | 5/2001 |
| JP | 2001-240245 | A | | 9/2001 |
| JP | 2005-249740 | A | | 9/2005 |
| JP | 2006-106008 | A | | 4/2006 |
| JP | 2007-309675 | A | | 11/2007 |
| JP | 2007-314262 | A | | 12/2007 |
| JP | 2007-322289 | A | | 12/2007 |
| JP | 2009-036643 | A | | 2/2009 |
| JP | 2009-062188 | A | | 3/2009 |
| JP | 2009-145188 | A | | 7/2009 |
| JP | 2009-300402 | A | | 12/2009 |
| JP | 2010-243310 | A | | 10/2010 |
| JP | 2013-172009 | A | | 9/2013 |
| JP | 2013-190400 | A | | 9/2013 |
| SU | 685591 | A1 | | 9/1979 |
| WO | 96/36437 | A1 | | 11/1996 |
| WO | 03/042048 | A3 | | 5/2003 |
| WO | 2007024540 | A1 | | 3/2007 |
| WO | 2008/133708 | A1 | | 11/2008 |
| WO | 2009/002358 | A1 | | 12/2009 |
| WO | 2010/042722 | A1 | | 4/2010 |
| WO | 2012/170636 | A1 | | 7/2010 |
| WO | 2010/087303 | A1 | | 8/2010 |
| WO | 2010/129715 | A1 | | 11/2010 |
| WO | 2011/138448 | A1 | | 11/2011 |
| WO | 2012/158520 | A1 | | 11/2012 |
| WO | 2012/158541 | A1 | | 11/2012 |
| WO | 2013/064656 | A1 | | 5/2013 |
| WO | 2013/099647 | A1 | | 7/2013 |
| WO | 2013/152089 | A1 | | 10/2013 |
| WO | 2013/169778 | A1 | | 11/2013 |
| WO | 2013/177163 | A1 | | 11/2013 |
| WO | 2014/059134 | A1 | | 4/2014 |
| WO | 2014/071214 | A1 | | 5/2014 |

OTHER PUBLICATIONS

English translation of EP0601213, machine generated, 6 pages.
English translation of EP0775650, machine generated, 4 pages.

* cited by examiner 10
11
32
30
31
70
50
80
81

51
60
61
63
62
Y
X
40

SYSTEM FOR TRANSPORTING CONTAINERS BETWEEN DIFFERENT STATIONS AND A CONTAINER CARRIER

BACKGROUND

The present disclosure relates to a system for transporting containers between different stations and a container carrier.

There is a need for a system for transporting containers between different stations and a container carrier, in which the system and container carrier provide a high transport capacity combined with, at the same time, high flexibility, to, for example, transport certain containers with priority between different stations.

SUMMARY

According to the present disclosure, a system for transporting containers between different stations of a laboratory analysis system is presented. The containers are accommodated in container carriers. The system comprises a control unit for controlling the transport of the container carriers and a transport area divided into subareas. The subareas adjoining stations serve as transfer areas to the stations and on which the container carriers can be movably arranged. The system also comprises drives. The drives are activated by the control unit and each drive is assigned to a respective subarea. Each drive applies a drive force to an associated container carrier.

In accordance with one embodiment of the present disclosure, a container carrier for receiving containers is also disclosed. The container carrier is configured for use in the above system.

Accordingly, it is a feature of the embodiments of the present disclosure to provide a system for transporting containers between different stations and also a container carrier, in which the system and container carrier provide a high transport capacity combined with, at the same time, high flexibility, to transport certain containers with priority between different stations. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
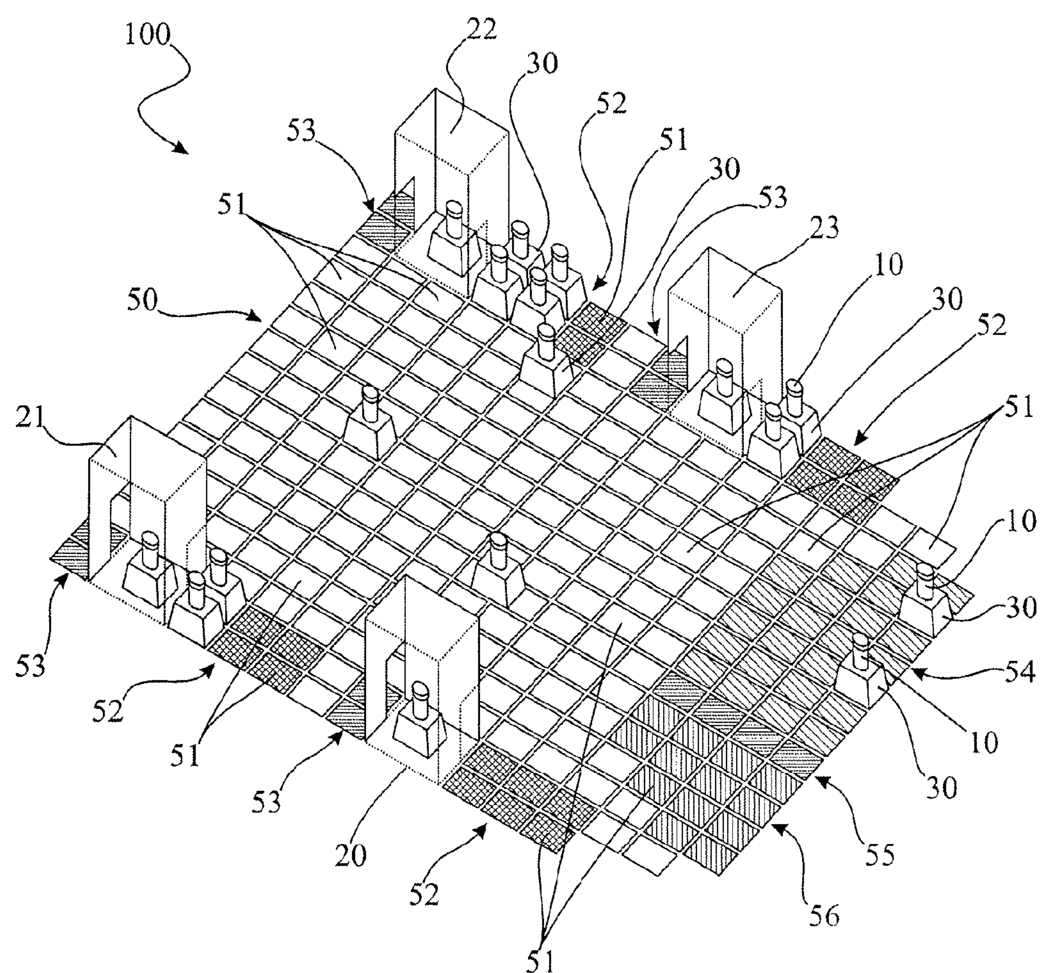
FIG. 1 illustrates a perspective view of a system for transporting containers between different stations according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

In the system for transporting containers between different stations, the containers such as, for example, sample containers of a laboratory analysis system, can be accommodated in container carriers, in that they can be inserted, for example, in an opening of the container carrier. The system can comprise a control unit such as, for example, a PC, which can control the transport of the container carriers. In addition, a transport area, or two-dimensional (2D) area divided into functional subareas, can be provided. In one embodiment, the transport area can be flat and horizontal. The transport area can be rectangular, for example, or can have any other suitable shape. The container carriers can be arranged on the transport area such that they can freely move. Stations can be arranged adjoining the transport area or above the transport area. Subareas which adjoin stations can serve as transfer areas to the stations.

The system can further comprise drives which can be activated by the control unit. Each drive can be assigned to a respective subarea. The drives apply a drive force to an associated container carrier, that is, a container carrier which is located on a subarea to which the drive is assigned, or an adjacent subarea, or within an operating range of the drive, in the direction of the transport area plane. The splitting of the transport area into subareas having their own drive leads to a high number of degrees of motional freedom of the container carriers, that is, the container carriers, barring inadmissible collisions, can be moved freely or on a subarea granular basis on the transport area. This can enable paths, for instance, which can be specific to the container carrier, and thus, for example, an accelerated transport of specific containers or container carriers between the stations.

In one embodiment, each drive applies the drive force to an associated container carrier in a contactless manner, that is, without direct mechanical contact between the drive and container carrier.

In one embodiment, each drive can generate the drive force alternatively in a first, a second, a third, or at least a fourth direction, wherein the directions respectively differ. In one embodiment, the second direction can be perpendicular to the first direction, the third direction can be opposite to the first direction, and the fourth direction can be opposite to the second direction. The directions, that is, the drive force vectors, can lie, in one embodiment, in a plane parallel to a transport area plane.

In one embodiment, the transport area can comprise at least one transport area region divided into grid areas of identical size. The grid areas can at least partially form the subareas. In one exemplary embodiment, the grid areas can be rectangles. In one embodiment, the transport area can comprise a plurality of transport area regions. Each respective transport area region can be divided into equal-sized grid areas. The sizes of the grid areas of different transport area regions can differ. This can enable, for instance, a rapid transport of the container carriers in transport area regions having more coarsely gridded, that is, larger subareas and a higher positional accuracy in transport area regions having more finely gridded, that is smaller, subareas.

In one embodiment, the container carriers can comprise magnetic, or ferromagnetic material, having permanent or non-permanent magnetization. The drives can generate a variable magnetic field in order to apply the drive force to an associated container carrier in a contactless manner.

In one embodiment, each drive can comprises four coils for generating a magnetic field. In one exemplary embodiment, the four coils are without a ferromagnetic core. In one embodiment, the control unit applies a current simultaneously to two of the four coils in order to generate the drive force or a suitable magnetic field. In one embodiment, the coils can be arranged such that their winding axes form a parallelogram. In one embodiment, the parallelogram can be a rectangle. In another embodiment, the parallelogram can be a square. The parallelogram can lie in a plane parallel to the transport area plane.

In one embodiment, the drives can apply the drive force to an associated container carrier by compressed air.

In one embodiment, the drives can be beneath the transport area.

In one embodiment, the containers and/or the container carriers can have passive, or active (RFID), transponders. The system can comprise at least one transponder reader designed to perform identification of the container and/or of the container carrier and also a position fixing of the container and/or of the container carrier on the transport area. In one embodiment, the system can generate an air cushion on the transport area in order to enable movement of the container carriers on the transport area as frictionless as possible. The container carrier can receive containers. The container carrier can comprise portions, or inserts, made of ferromagnetic material. In one embodiment, the portions can be on bottom side of the container carrier, that is, on the side that faces the transport area, or in a lower region.

In one embodiment, the container carrier can receive containers in the form of sample containers containing samples to be analyzed, for example, samples of body fluids.

In one embodiment, the container carrier can be a drive-free container carrier, that is, a container without an active drive of its own. In one embodiment, the container carrier can contain no energy store of its own which can be used for its drive. In one embodiment, the container carrier can comprise a transponder.

A complete sample distributing system or laboratory analysis system can comprise, for instance, the above transport system, the stations and a plurality of abovementioned container carriers.

Referring initially to FIG. 1, a schematic, perspective view of a system 100 for transporting containers 10 between different stations 20, 21, 22 and 23 is illustrated. The stations 20, 21, 22 and 23 can be different stations of a sample analysis system for medical samples. Samples to be analyzed, for example, body fluids 11 (see FIG. 2) such as blood or urine, can be supplied externally in the containers in the form of sample tubes 10 sealed with stoppers. The sample tubes can be accommodated in drive-free container carriers 30. The stations 20, 21, 22 and 23 can fulfill the functions which usually arise in this sample context. For example, one station can serve to remove the stopper from the sample tubes, a further station can be used for aliquoting purposes, a further station can perform a first sample analysis, or further stations can perform any other suitable function.

The system 100 can transport the sample tubes 10 between the different stations 20, 21, 22 and 23. The containers, or sample tubes, 10 can be, first, in each case with the associated container carrier 30, manually or mechanically disposed in an input region 54, formed from subareas 51, of the transport area 50. From the input region 54, the sample tubes 10 or the container carriers 30 can be transported by the system 100 to the stations 20, 21, 22 and 23, can be appropriately processed there and can next be transported to an output region 56 formed from subareas 51, from where they can be manually, or mechanically, removed from the transport area 50.

For the prioritized processing of emergency samples which are to be analyzed within a predefined maximum period, there can be an emergency input region 55, formed from subareas 51, into which the associated container carrier 30 containing the sample tubes 10 to be processed on a prioritized basis can be disposed.

The system can comprise a control unit 40 (see FIG. 3) such as, for example, a PC as the process computer, controlling the transport of the container carriers 30, the transport area 50 divided on a grid-like basis into square subareas, or grid areas, 51 of identical size and on which the container carriers 30 can be movably arranged, and a plurality of drives, wherein each drive of the plurality of drives can be assigned to a respective subarea 51 and each drive can apply a drive force to an associated container carrier 30. The transport area 50 can be fully split into subareas 51, wherein, for reasons of illustration, only example subareas are shown with the reference symbol 51.

Figure 3:
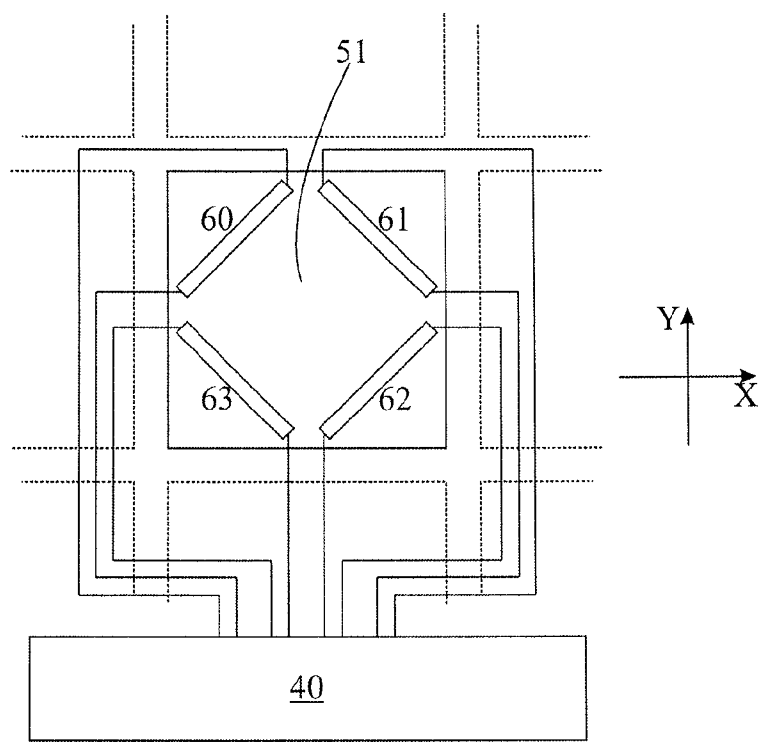
FIG. 3 illustrates a schematic top view of a subarea and an associated drive of the systems shown in FIGS. 1 and 2 according to an embodiment of the present disclosure.

FIG. 3 shows a schematic top view of an example part area 51 and an associated drive. With reference to FIG. 3, beneath the example subarea 51 four coils 60, 61, 62, 63 without ferromagnetic core can be disposed forming the associated drive of the example subarea 51. The coils 60, 61, 62, 63 can be arranged such that their winding axes form a square. The square can lie in a plane parallel to the transport area 50 or to a transport area plane formed by the transport area 50. Each subarea 51 can be assigned a corresponding drive, or coils. The control unit 40 can apply a current to two of the four coils 60, 61, 62, 63 in order to generate a magnetic field or a drive force.

Figure 2:
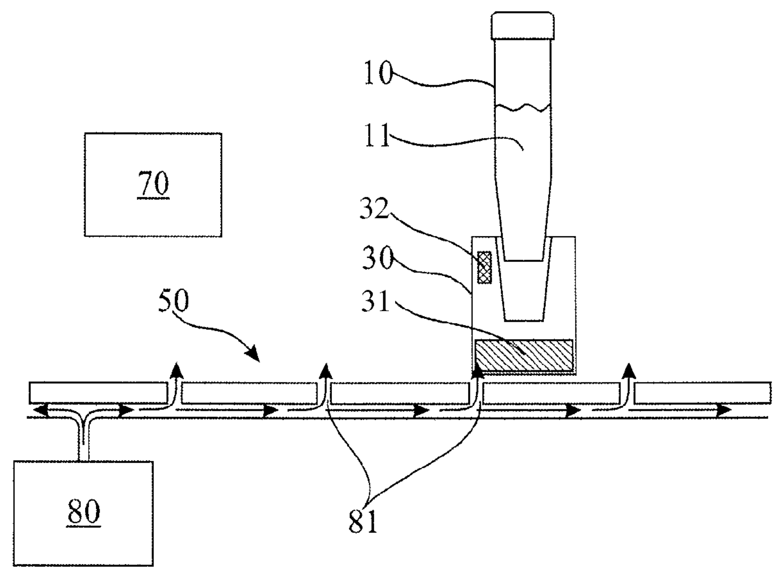
FIG. 2 illustrates a side view of the system shown in FIG. 1 according to an embodiment of the present disclosure.

With reference to FIG. 2, the container carrier 30 can comprise, on its bottom side, portions made of ferromagnetic material 31, or a permanent magnet, whereby, due to the magnetic field generated by the coils 60, 61, 62, 63, the drive force can be applied to the container carrier 30 in a contactless manner.

By energizing the coils 60, 61, 62, 63, the magnetic field, or the drive force, can be generated in a first, a second, a third or at least a fourth direction. A simultaneously energized coil pair can be formed, for instance, by the coils (60, 63), (62, 63), (61, 62) and (60, 61). The direction of the drive force can be inverted by reversing the polarity of the current feed.

A container carrier 30 can, for example, be pushed from the subarea 51 by a generated drive force and/or can be pulled to the adjacent subarea by a drive force which can be generated by the drive of an adjacent subarea. Just a single drive of a single subarea can be involved in the movement, or drive, of a container carrier 30 or a plurality of drives of a plurality of subareas can be involved. The drives can simultaneously also serve to slow down and/or fix the container carriers 30.

Subarea regions 52 formed from subareas 51 and adjoin the stations 20, 21, 22, 23 can serve as transfer areas to the stations, that is, as waiting lines. Subarea regions 53 formed from subareas 51 and adjoin the stations 20, 21, 22, 23 on another side can serve as prioritized transfer areas to the stations, for example, as waiting lines for emergency samples. All functional subarea regions 52, 53, 54, 55 and 56 can be formed from a predefined number of subareas 51.

FIG. 2 shows a side view of the system 100 shown in FIG. 1. With reference to FIG. 2, a compressed air generator 80 can generate compressed air which can be guided via a suitable supply to the transport area 50 where it can be discharged via openings 81 in the transport area 50. The compressed air generator 80 and the openings 81 can serve to generate an air cushion on the transport area 50 in order to enable movement of the container carriers 30 on the transport area 50 as frictionless as possible. The openings 81 can be distributed over the transport area 50. In one embodiment, the openings 81 can be distributed evenly over the transport area 50. Alternatively or additionally, a friction reduction can also be realized magnetically. A magnetic field with vertical components can be generated so as to reduce a contact pressure of the container carrier 30 on the transport area 50 or effect a floating of the container carrier 30. In one embodiment, the magnetic field can be generated dynamically. A further embodiment for reducing friction can be to coat the transport area 50 and/or the bottom sides or slide surfaces of the container carriers 30 with a low-friction coating such as, for example, Teflon. In this embodiment, the generation of an air cushion may be omitted.

The container carriers 30 can have transponders 32. The system 100 can comprise at least one transponder reader 70 to perform an identification of the container carrier 30 and a position fixing of the container carrier 30 on the transport area 50. If at least three transponder readers 70, for example, are contained in the system 100, a position fixing can be realized by triangulation.

In the system 100, the transport area 50 can comprise one transport area region identical to the transport area 50 and divided into equal-sized grid areas. The grid areas can form the subareas 51. Alternatively, the transport area 50 can comprise a plurality of transport area regions. The transport area region can be divided into equal-sized grid areas. The sizes of the grid areas of different transport area regions can differ. This can enable, for example, a rapid transport of the container carriers 30 in transport area regions having more coarsely gridded, that is larger, subareas 51 and a higher positioning accuracy in transport area regions having more finely gridded, that is smaller, subareas 51.

In one embodiment, a container carrier 30, with its bottom side facing the transport area 50, can substantially fully cover a subarea 51. In the case of different-sized subareas 51, the bottom side of the container carrier 30 can also cover a plurality of subareas, in which event the drives of a plurality of subareas 51 can generate drive force contributions, which can be superimposed one upon the other to form a resulting drive force.

In one embodiment, the drive force can be generated electromagnetically. Alternatively or additionally, it can be possible to pressurize a container carrier 30 by compressed air for the generation of the drive force.

The illustrated embodiments can enable a high transport capacity combined with, at the same time, high flexibility, in order, for instance, to transport emergency samples between different stations.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory analysis system, the system comprising:

a plurality of containers containing samples to be analyzed;

a plurality of container carriers for receiving the containers, each container carrier includes a ferromagnetic material;

a plurality of different stations for analyzing the samples; and a system for transporting the container carriers between different stations, the system for transporting the container carriers comprising:

a control unit for controlling the transport of the container carriers;

a plurality of drives, wherein the drives are activated by the control unit, wherein each drive generates a variable magnetic field to apply a drive force to an associated container carrier, a transport area, wherein each drive is assigned to a respective subarea of the transport area creating a path, wherein subareas adjoining stations serve as transfer areas to the stations, wherein the container carriers can be movably arranged on the transport area, wherein the containers or the container carriers include transponders, wherein the system further includes at least three transponder readers configured to perform identification of the container or container carrier and position fixing of the container or container carrier by triangulation performed by the controller.

2. The system according to claim 1, wherein the plurality of different stations comprise a station for removing a stopper from sample tubes, a station for aliquoting, a station for sample analysis or combinations thereof.

3. The system according to claim 1, wherein each drive applies the drive force to the associated container carrier in a contactless manner.

4. The system according to claim 1, wherein each drive generates the drive force alternatively in a first, a second, a third, or a fourth direction.

5. The system according to claim 1, wherein the transport area comprises at least one transport area region divided into equal-sized grid areas and wherein the grid areas at least partially form the subareas.

6. The system according to claim 1, wherein the transport area comprises a plurality of transport area regions, wherein each transport area region is divided into equal-sized grid areas, and wherein the sizes of the grid areas of different transport area regions differ.

7. The system according to claim 1, wherein each drive comprises four coils.

8. The system according to claim 7, wherein each drive comprises four coils without a ferromagnetic core.

9. The system according to claim 7, wherein the control unit applies a current to two of the four coils in order to generate the drive force.

10. The system according to claim 7, wherein the coils are arranged such that their winding axes form a parallelogram, wherein the parallelogram lies in a plane parallel to the transport area.

11. The system according to claim 1, wherein the drives are beneath the transport area.

* * * * *